(12) United States Patent
Sako

(10) Patent No.: US 10,514,346 B2
(45) Date of Patent: Dec. 24, 2019

(54) X-RAY FLUORESCENCE SPECTROMETER

(71) Applicant: RIGAKU CORPORATION, Tokyo (JP)

(72) Inventor: Yukio Sako, Osaka (JP)

(73) Assignee: RIGAKU CORPORATION, Tokyo (JP)

(*) Notice: Subject to any disclaimer, the term of this patent is extended or adjusted under 35 U.S.C. 154(b) by 0 days.

(21) Appl. No.: 16/465,661

(22) PCT Filed: Nov. 21, 2017

(86) PCT No.: PCT/JP2017/041896
§ 371 (c)(1),
(2) Date: May 31, 2019

(87) PCT Pub. No.: WO2018/101133
PCT Pub. Date: Jun. 7, 2018

(65) Prior Publication Data
US 2019/0302041 A1    Oct. 3, 2019

(30) Foreign Application Priority Data
Dec. 1, 2016  (JP) ................. 2016-234455

(51) Int. Cl.
*G01N 23/00*    (2006.01)
*G01N 23/223*   (2006.01)
*G01N 23/207*   (2018.01)

(52) U.S. Cl.
CPC ........ *G01N 23/223* (2013.01); *G01N 23/2076* (2013.01); *G01N 2223/076* (2013.01)

(58) Field of Classification Search
CPC ............. G01N 23/223; G01N 23/2076; G01N 2223/076
See application file for complete search history.

(56) References Cited

U.S. PATENT DOCUMENTS 5,978,442 A * 11/1999 Kuwabara ............... G01N 23/20
                                                          378/46
7,720,192 B2 * 5/2010 Hegeman ............. G01N 23/223
                                                          378/44

FOREIGN PATENT DOCUMENTS

EP    0 766 083 A2    4/1997
JP    S59-214743 A    12/1984
(Continued)

OTHER PUBLICATIONS

International Search Report of PCT/JP2017/041896 dated Feb. 20, 2018.
(Continued)

*Primary Examiner* — Dani Fox
(74) *Attorney, Agent, or Firm* — Brinks Gilson & Lione

(57) ABSTRACT

Provided is an X-ray fluorescence spectrometer, which has a simple structure, and is capable of promptly performing high-accuracy analysis. The X-ray fluorescence spectrometer according to the present invention includes: an X-ray source (100) configured to irradiate a sample (103) with primary X-rays; a spectroscopic device (120) configured to disperse secondary X-rays emitted from the sample (103); an energy-dispersive detector (110) configured to measure an intensity of the secondary X-rays; a retracting mechanism (108) configured to retract the spectroscopic device (120) from a path of the secondary X-rays; a scanning mechanism (114), which is configured to continuously move the detector (110) between an auxiliary measurement area (124) for measuring the secondary X-rays in a state where the spectroscopic device (120) is retracted and a main measurement area (122) for measuring the dispersed secondary X-rays; a storage device (116) configured to store, in advance, a ratio between a background intensity measured in the auxiliary measurement area (124) and a background intensity measured in the main measurement area (122); and an arithmetic (Continued)

device (118) configured to perform correction and quantitative analysis, the correction including subtracting a value, which is obtained by multiplying the background intensity in the auxiliary measurement area (124) by the ratio, from a measured intensity in the main measurement area (122).

8 Claims, 5 Drawing Sheets

(56) References Cited

FOREIGN PATENT DOCUMENTS

| | | |
|---|---|---|
| JP | H 10-206356 A | 8/1998 |
| JP | 2000-292382 A | 10/2000 |
| JP | 2000-329714 A | 11/2000 |
| JP | 2008-256698 A | 10/2008 |

OTHER PUBLICATIONS

Sako, Yukio, "Notification of Reasons for Refusal" of JP 2018-526963, dated Jun. 21, 2018, machine translated Apr. 1, 2019.

\* cited by examiner (a)

(b)

X-RAY FLUORESCENCE SPECTROMETER

CROSS-REFERENCE TO RELATED APPLICATIONS

This application is a 35 U.S.C. § 371 national phase of PCT International Application No. PCT/JP2017/041896, filed Nov. 21, 2017, which claims the benefit of priority under 35 U.S.C. § 119 to Japanese Patent Application No. 2016-234455, filed Dec. 1, 2016, the contents of which are incorporated herein by reference in their entirety.

FIELD OF THE INVENTION

The present invention related to an X-ray fluorescence spectrometer.

BACKGROUND

An X-ray fluorescence spectrometer has been known as an instrument for measuring elements contained in a sample and the concentration of the elements. The X-ray fluorescence spectrometer is configured to detect fluorescent X-rays emitted from a sample when the sample is irradiated with X-rays and analyze constituent elements based on the energy and an intensity of the fluorescent X-rays.

An energy-dispersive X-ray fluorescence spectrometer and a wavelength-dispersive X-ray fluorescence spectrometer have been widely used as the X-ray fluorescence spectrometer. The energy-dispersive X-ray fluorescence spectrometer is equipped with an energy-dispersive detector and can analyze all the elements at the same time. The wavelength-dispersive X-ray fluorescence spectrometer is configured to disperse X-rays using a spectroscopic device for each element and can perform analysis more accurately compared to the energy-dispersive spectrometer.

Specifically, the wavelength-dispersive X-ray fluorescence spectrometer has an energy resolution of about 10 eV through the use of the spectroscopic device. Meanwhile, the energy-dispersive X-ray fluorescence spectrometer without using the spectroscopic device performs analysis through the use of a semiconductor detector, for example, a silicon drift detector (SDD) having an energy resolution of about 100 eV.

In the energy-dispersive spectrometer, there are a larger number of peak overlaps of measurement lines and a background intensity is higher compared to the wavelength-dispersive spectrometer. Therefore, in general, the energy-dispersive spectrometer removes the background intensity by, for example, waveform separation processing and extracts only a peak intensity to thereby perform quantitative analysis.

Meanwhile, in the wavelength-dispersive spectrometer, separation and removal of a background intensity are not performed in general since the influence of the background intensity is smaller compared to the energy-dispersive spectrometer. However, when performing high-accuracy analysis, for example, quantitative analysis of minor components, separation and removal of the background intensity are performed through the use of the wavelength-dispersive spectrometer in some cases.

For example, in a general sequential spectrometer configured to perform scanning with a goniometer through interlocking of a spectroscopic device and a detector, a background intensity is measured at around a peak region by moving the goniometer under the assumption that the sensitivity of the measurement of the background at the peak region is almost the same as that at around the peak region and then quantitative analysis is performed by subtracting the background intensity from a measured peak intensity. In this case, it takes a long period of time for the measurement.

Further, in JP 10-206356 A, there is the following disclosure. Both a detector configured to measure secondary X-rays from a sample dispersed by a spectroscopic device and an energy-dispersive detector configured to directly measure the secondary X-rays from the sample without dispersing the secondary X-rays are mounted in a wavelength-dispersive spectrometer, and the detectors to be used are switched in accordance with the application.

However, the configuration including both the energy-dispersive detector configured to directly measure the secondary X-rays from the sample without dispersing the secondary X-rays and the detector configured to measure the secondary X-rays dispersed by the spectroscopic device increases the complexity of the instrument.

In view of the foregoing, for example, in JP 2000-292382 A and JP 2000-329714 A, as an X-ray fluorescence spectrometer having a simple device configuration, there is a disclosure of an X-ray fluorescence spectrometer including both a spectroscopic device configured to disperse secondary X-rays and an energy-dispersive detector configured to measure the dispersed X-rays. For example, this spectrometer is configured to first directly measure secondary X-rays emitted from a sample and obtain a full energy spectrum in a short period of time, and then measure the dispersed secondary X-rays. Accordingly, the spectrometer individually measure fluorescent X-rays of minor elements and fluorescent X-rays that cannot be separated from an interfering line without being dispersed.

Further, a technology of removing the above-mentioned background intensity is, for example, described in the following JP 2008-256698 A. An X-ray intensity within a narrow energy range is measured while secondary X-rays dispersed by a spectroscopic device are scanned with an energy-dispersive detector over a wide spectroscopic angle (energy) range. A background intensity due to interference of, for example, neighboring lines and higher-order X-rays at a peak angle (energy) is estimated based on the measured X-ray spectrum, and the estimated background intensity is subtracted from a measured peak in the X-ray spectrum.

SUMMARY OF INVENTION

Technical Problem

Although general analysis can be performed promptly by the X-ray fluorescence spectrometer which has both the spectroscopic device and the energy-dispersive detector and uses them differently depending on the measurement as described in JP 10-206356 A and JP 2000-329714 A, it takes a long period of time for measurement when high-accuracy analysis by removing a background intensity is performed because it is required to measure a peak intensity and a background intensity individually as described above.

Further, it is difficult to sufficiently remove a background having the same energy as a peak when the energy-dispersive detector is scanned with a goniometer over a wide energy range to measure dispersed secondary X-rays and then a background intensity is estimated based on the measured spectrum as described in JP 2008-256698 A.

Further, since the intensity of the background is lower than that of the peak and the sensitivity is too low to measure the background with sufficient accuracy when the secondary X-rays dispersed by the spectroscopic device are measured with the energy-dispersive detector, long measurement times are required. In addition, as a longer period of time is required when measurement is performed over a wider spectroscopic angle (energy) range, prompt analysis cannot be performed.

The present invention has been made in view of the above-mentioned problems, and an object of the present invention is to provide an X-ray fluorescence spectrometer, which has a simple structure and can promptly perform high-accuracy analysis by removing a background intensity.

Solution to Problem

An X-ray fluorescence spectrometer according to claim 1 includes: an X-ray source configured to irradiate a sample with primary X-rays; a spectroscopic device configured to disperse secondary X-rays emitted from the sample; an energy-dispersive detector configured to measure an intensity of the secondary X-rays; a retracting mechanism configured to retract the spectroscopic device from a path of the secondary X-rays; a scanning mechanism, which is configured to continuously move the energy-dispersive detector between an auxiliary measurement area for measuring the secondary X-rays in a state where the spectroscopic device is retracted by the retracting mechanism and a main measurement area for measuring the secondary X-rays dispersed by the spectroscopic device, and is configured to change an angle of the spectroscopic device so that the secondary X-rays dispersed by the spectroscopic device enter the energy-dispersive detector in the main measurement area; a storage device configured to store, in advance, a ratio between a background intensity of the secondary X-rays measured in the auxiliary measurement area and a background intensity of the secondary X-rays dispersed by the spectroscopic device, which is measured in the main measurement area; and an arithmetic device, which is configured to calculate a background intensity included in a measured intensity in the auxiliary measurement area through waveform separation, and is configured to perform correction and quantitative analysis, the correction including subtracting a value, which is obtained by multiplying the calculated background intensity corresponding to energy of an analysis line by the ratio, from a measured intensity of the analysis line in the main measurement area.

In an X-ray fluorescence spectrometer according to claim 2, in the X-ray fluorescence spectrometer according to claim 1, the scanning mechanism is configured to move the energy-dispersive detector to a position where the secondary X-rays emitted from the sample directly enter into the auxiliary measurement area.

In an X-ray fluorescence spectrometer according to claim 3, in the X-ray fluorescence spectrometer according to claim 1, further includes a total reflection mirror, which is configured to remove a high energy component, and is arranged at a position from which the spectroscopic device is retracted, wherein the storage device is configured to store, in advance, a ratio between a background intensity of the secondary X-rays reflected by the total reflection mirror, which is measured in the auxiliary measurement area, and a background intensity of the secondary X-rays dispersed by the spectroscopic device, which is measured in the main measurement area.

In an X-ray fluorescence spectrometer according to claim 4, in the X-ray fluorescence spectrometer according to any one of claims 1 to 3, the spectroscopic device includes a plurality of spectroscopic devices configured to disperse the secondary X-rays having different wavelengths, wherein the storage device is configured to store the different ratio depending on the spectroscopic devices.

In an X-ray fluorescence spectrometer according to claim 5, in the X-ray fluorescence spectrometer according to any one of claims 1 to 4, the storage device is configured to store the ratio corresponding to energy of the secondary X-rays.

In an X-ray fluorescence spectrometer according to claim 6, in the X-ray fluorescence spectrometer according to any one of claims 1 to 5, the storage device is configured to store the ratio as a function of the energy of the secondary X-rays.

In an X-ray fluorescence spectrometer according to claim 7, in the X-ray fluorescence spectrometer according to claims 1 to 6 uses a reference sample free of elements to be analyzed when measuring the ratio to be stored in the storage device.

In an X-ray fluorescence spectrometer according to claim 8, in the X-ray fluorescence spectrometer according to claim 7, the reference sample includes graphite or an acrylic resin.

Advantageous Effects of Invention

According to the present invention, the ratio of the background intensity between the secondary X-rays dispersed by the spectroscopic device and the secondary X-rays measured without being dispersed is stored in advance through the use of one energy-dispersive detector. As a result, high-accuracy analysis by removing the background intensity can be promptly performed without measuring the secondary X-rays dispersed by the spectroscopic device over the peak adjacent region and the wide energy range, and the configuration of the X-ray fluorescence spectrometer can be made simple.

DETAILED DESCRIPTION

Now, a preferred embodiment (hereinafter referred to as "embodiment") of the present invention is described with reference to the drawings.

Figure 1:
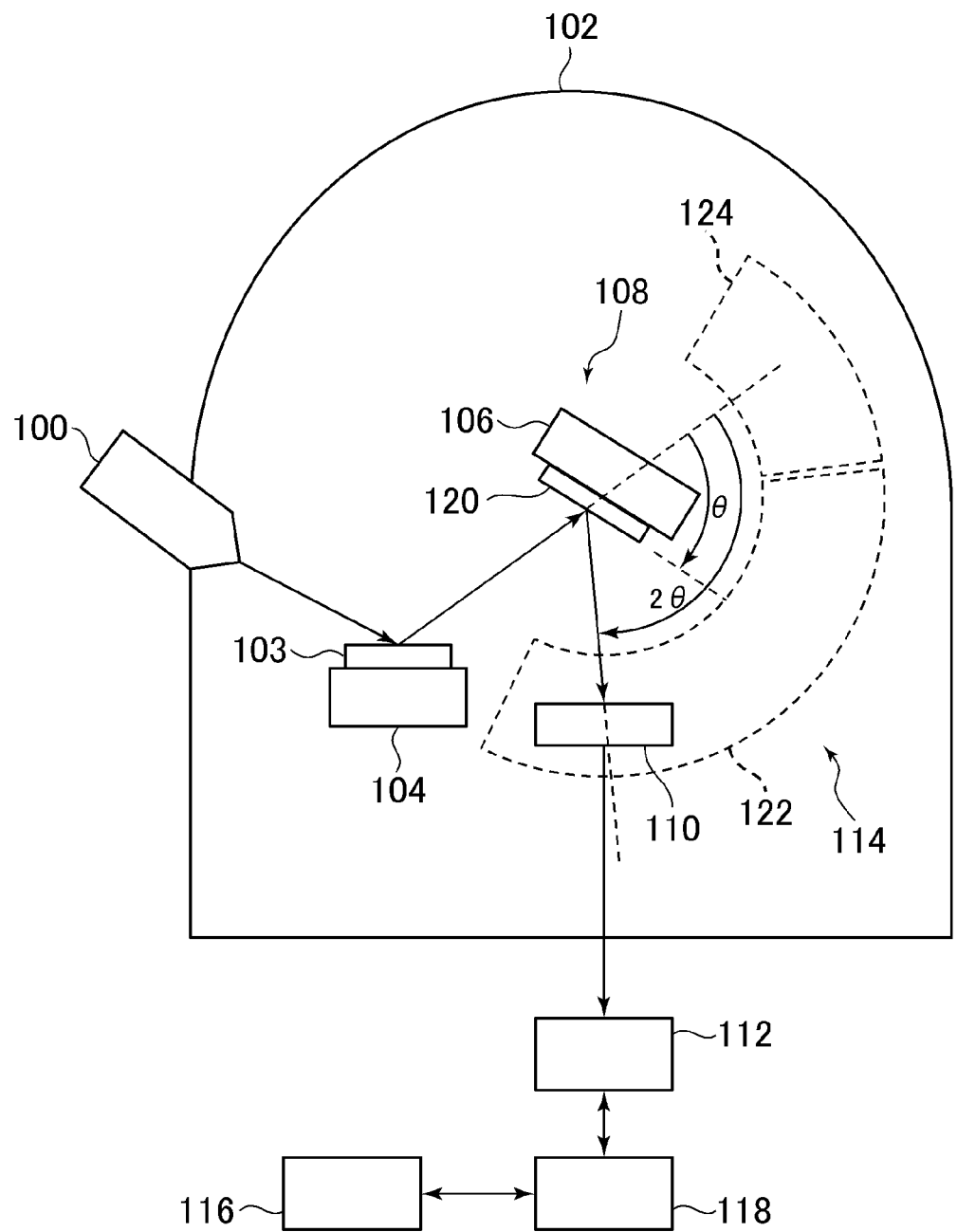
FIG. 1 is a diagram for schematically illustrating an X-ray fluorescence spectrometer in the embodiment of the present invention.

FIG. 1 is a diagram for schematically illustrating an X-ray fluorescence spectrometer in the embodiment of the present invention. As illustrated in FIG. 1, the X-ray fluorescence spectrometer includes an X-ray source 100, a sample chamber 102, a sample stage 104, a spectroscopic device fixing stage 106, a retracting mechanism 108, a detector 110, a counter 112, a scanning mechanism 114, a storage device 116, and an arithmetic device 118.

The X-ray source 100 is configured to irradiate a sample 103 mounted on the sample stage 104 with primary X-rays.

The sample chamber 102 is configured to accommodate an emitting portion of the X-ray source 100, the sample stage 104, the spectroscopic device fixing stage 106, the retracting mechanism 108, the detector 110, and the scanning mechanism 114. Also, the inside of the sample chamber 102 may be evacuated by a vacuum pumping device (not shown). Further, the emitting portion of the X-ray source 100 and the sample chamber 102 configured to accommodate the sample stage 104 may be divided by a partition wall that transmits X-rays and a spectroscopic chamber (not shown) configured to accommodate the spectroscopic device fixing stage 106, the retracting mechanism 108, the detector 110, and the scanning mechanism 114 may be located.

The sample stage 104 is configured to mount the sample 103 thereon. Specifically, for example, the sample stage 104 is configured to mount the sample 103, which is to be measured, on a surface to be irradiated with the primary X-rays from the X-ray source 100. Further, for example, the sample stage 104 is configured to mount a reference sample on the surface to be irradiated with the primary X-rays from the X-ray source 100 in order to obtain measurement data required for calculating a ratio described later.

The spectroscopic device fixing stage 106 is configured to fix thereto a spectroscopic device 120. Specifically, for example, the spectroscopic device fixing stage 106 is configured to fix thereto the spectroscopic device 120 configured to disperse only a particular wavelength that satisfies a so-called Bragg's condition in accordance with an incident angle among secondary X-rays having a plurality of wavelengths emitted from the sample.

The spectroscopic device fixing stage 106 may be configured to fix thereto a plurality of spectroscopic devices 120 in order to disperse the secondary X-rays having different wavelengths or different wavelength bands. Specifically, for example, the spectroscopic devices 120 having different lattice spacings are fixed to different surfaces of the spectroscopic device fixing stage 106 having a polygonal column shape and the spectroscopic device fixing stage 106 is rotated about a center axis of the polygonal column by a spectroscopic device switching device (not shown) in order to select the spectroscopic device 120 depending on an element to be measured.

In order to obtain an adequate angular resolution of X-rays dispersed by the spectroscopic device 120, a slit (not shown) may be located between the sample and the spectroscopic device 120 and/or between the spectroscopic device 120 and the detector 110.

Figure 2:
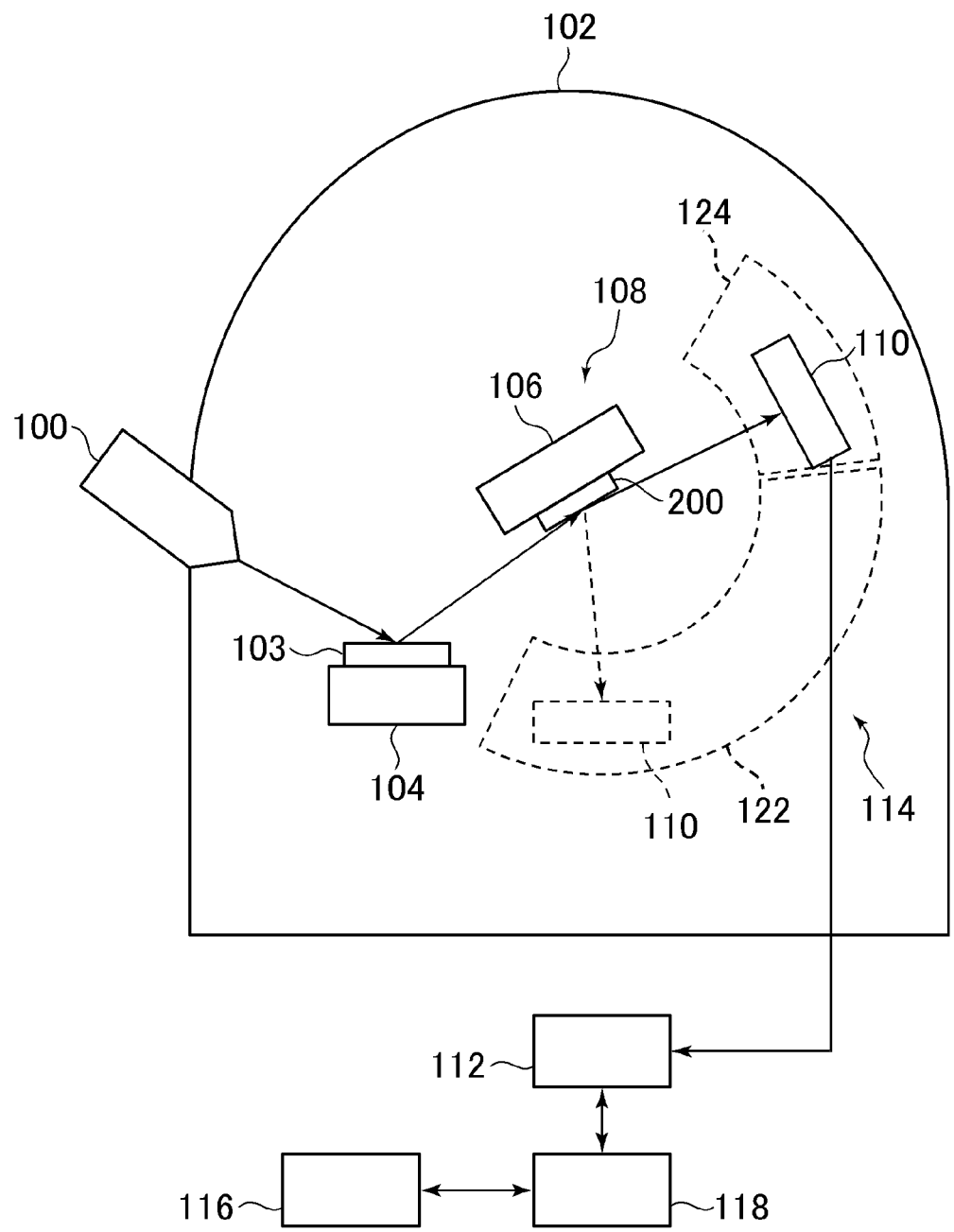
FIG. 2 is a diagram for schematically illustrating the X-ray fluorescence spectrometer with a total reflection mirror.

Further, the spectroscopic device fixing stage 106 may be configured to fix thereto a total reflection mirror 200. Specifically, for example, as illustrated in FIG. 2, the spectroscopic device fixing stage 106 may be configured to fix thereto the total reflection mirror 200 removing a high energy component. Also, one of the plurality of spectroscopic devices 120 fixed to the spectroscopic device fixing stage 106 may be replaced by the total reflection mirror 200, and the total reflection mirror 200 may be selected through the use of the spectroscopic device switching device.

Figure 3:
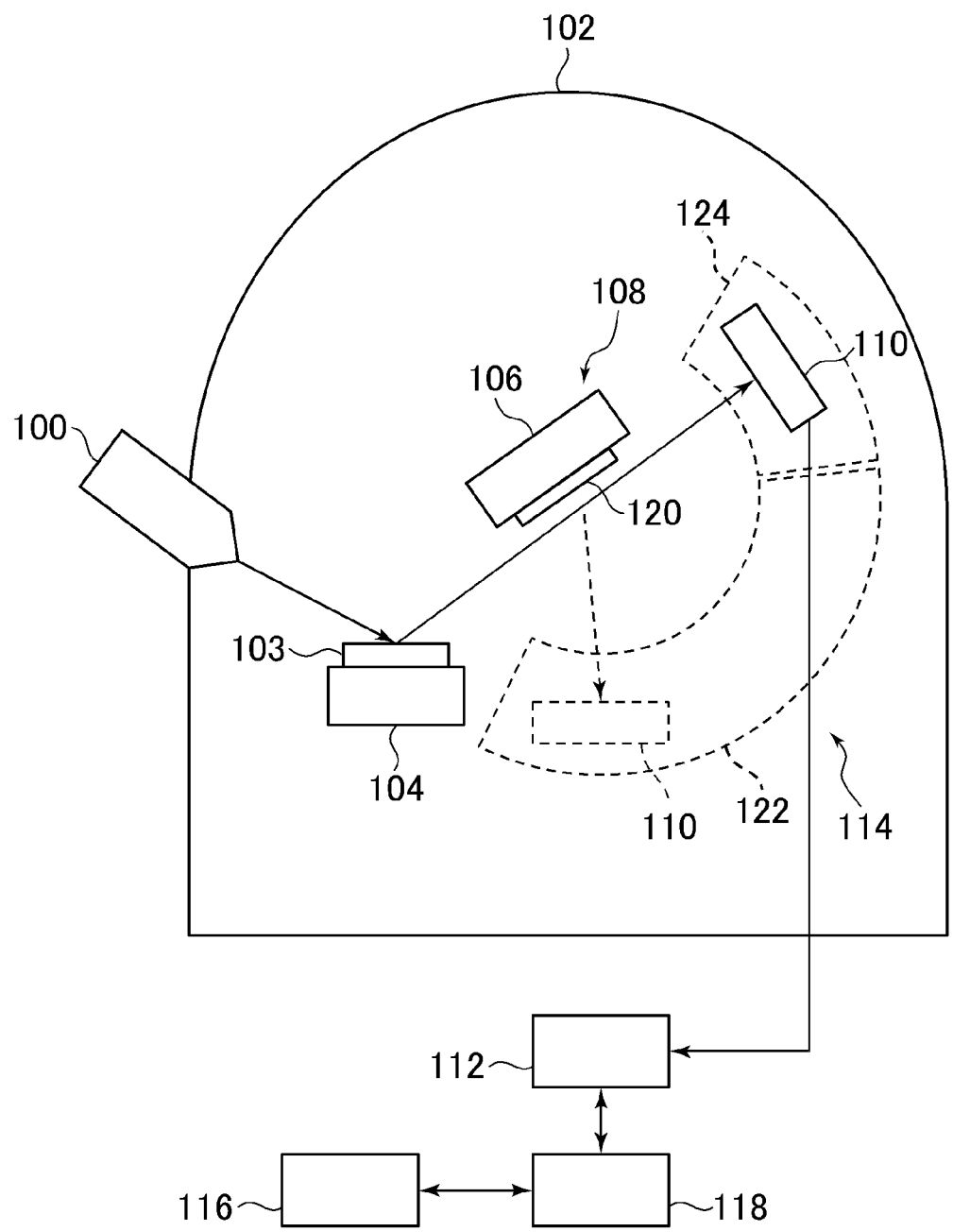
FIG. 3 is a diagram for schematically illustrating the X-ray fluorescence spectrometer with a retracted spectroscopic device.

The retracting mechanism 108 is configured to retract the spectroscopic device 120 from a path of the secondary X-rays. Specifically, for example, as illustrated in FIG. 3, the retracting mechanism 108 is configured to retract the spectroscopic device 120 from a path, through which the secondary X-rays emitted from the sample travel, by moving the spectroscopic device fixing stage 106 with the spectroscopic device 120 being fixed thereto. Alternatively, for example, the spectroscopic device 120 may be retracted as follows. The spectroscopic device switching device is used as the retracting mechanism 108, and the spectroscopic device fixing stage 106 is rotated so that a surface of the polygonal column on which the spectroscopic device is not mounted is selected. Thus, the spectroscopic device 120 is retracted to a position of not blocking the secondary X-rays emitted from the sample.

The scanning mechanism 114 is configured to continuously move the detector 110 between an auxiliary measurement area 124 and a main measurement area 122. In the auxiliary measurement area 124, the X-ray fluorescence spectrometer serves as an energy-dispersive spectrometer to measure the secondary X-rays in a state where the spectroscopic device 120 is retracted by the retracting mechanism 108. In the main measurement area 122, the X-ray fluorescence spectrometer serves as a wavelength-dispersive spectrometer to measure the secondary X-rays dispersed by the spectroscopic device 120.

Specifically, for example, at a time of measurement of an analysis sample, the scanning mechanism 114 continuously moves the detector 110 between the auxiliary measurement area 124 for measuring the secondary X-rays in order to obtain a background intensity and the main measurement area 122 for measuring the secondary X-rays in order to obtain a peak intensity of an element contained in the sample 103.

In this case, the auxiliary measurement area 124 is an area including a position where the secondary X-rays emitted from the sample directly enter in a state where the spectroscopic device 120 is retracted and a position where the secondary X-rays reflected by the total reflection mirror 200 enter. The total reflection mirror 200 is arranged at a position from which the spectroscopic device 120 is retracted.

Specifically, for example, when an incident angle formed by the traveling direction of the secondary X-rays emitted from the sample and the surface of the spectroscopic device 120 is $\theta$ degrees, the auxiliary measurement area 124 corresponds to a position at which $\theta$ is 0 degrees. Further, the position where the secondary X-rays reflected by the total reflection mirror 200 enter corresponds to a position at which $2\theta$ is in the vicinity of 0 degrees (for example, 0.5 degrees).

The main measurement area 122 is an area where the secondary X-rays dispersed by the spectroscopic device 120 enter. Specifically, for example, the main measurement area 122 is an area in which $2\theta$ is from 10 degrees to 160 degrees.

Further, the scanning mechanism 114 is configured to change an incident angle at which the secondary X-rays enter the spectroscopic device 120 and move the position of the detector 110 in a direction in which the dispersed secondary X-rays are emitted. Specifically, for example, when the incident angle is $\theta$ degrees, the scanning mechanism 114 rotates the spectroscopic device fixing stage 106 and moves the detector 110 so that an angle formed by the traveling direction of the secondary X-rays emitted from the sample and the traveling direction of the secondary X-rays dispersed by the spectroscopic device 120 becomes $2\theta$ degrees. The scanning mechanism 114 is, for example, a so-called goniometer.

Through the operation of the scanning mechanism 114, an incident angle at which the secondary X-rays enter the spectroscopic device 120 is changed. The incident angle is a function of energy of the secondary X-rays to be dispersed, and hence the detector 110 including the scanning mechanism 114 can measure an intensity of the secondary X-rays having various energies with a high energy resolution.

As described above, with the configuration in which the scanning mechanism 114 causes the detector 110 to perform scanning continuously at $\theta$ of from 0 degrees to 160 degrees or to move at any angle, a mechanism configured to perform measurement in the auxiliary measurement area 124 and a mechanism configured to perform measurement in the main measurement area 122 can be shared, and the configuration of the X-ray fluorescence spectrometer can be made simple.

The detector 110 is an energy-dispersive detector configured to measure an intensity of the secondary X-rays. Specifically, for example, the detector 110 is a semiconductor detector, for example, an SDD that has hitherto been known. The detector 110 may be a detector other than the semiconductor detector as long as the detector can be used as a detector of an energy-dispersive X-ray fluorescence spectrometer and has an energy resolution with which element analysis can be performed. Further, the detector 110 is arranged by the scanning mechanism 114 at a position where the secondary X-rays directly enter, a position where the secondary X-rays reflected by the total reflection mirror 200 enter, or a position where the dispersed secondary X-rays enter.

The counter 112 is configured to count a pulse signal output from the detector 110 in accordance with a pulse height corresponding to the energy of the secondary X-rays and output the result to the arithmetic device 118. Specifically, for example, the counter 112 is a multichannel analyzer, which is configured to count an output pulse signal of the detector 110 for each channel corresponding to the energy and output the result to the arithmetic device 118 as an intensity of the secondary X-rays.

The storage device 116 is configured to store, in advance, a ratio between the background intensity measured in the auxiliary measurement area 124 and the background intensity measured in the main measurement area 122 with the sample 103 being an object to be measured.

Further, for example, the storage device 116 may store, in advance, a ratio between the background intensity of the secondary X-rays reflected by the total reflection mirror 200 and the background intensity measured in the main measurement area 122 when the reference sample is set to an object to be measured. A method of calculating a ratio and the arithmetic device 118 are described later in detail.

The arithmetic device 118 is configured to calculate a background intensity based on a measured intensity in the auxiliary measurement area through waveform separation, and is configured to perform correction and quantitative analysis, the correction including subtracting a value, which is obtained by multiplying the calculated background intensity corresponding to energy of an analysis line by the ratio, from a measured intensity of the analysis line in the main measurement area.

Specifically, at the time of analysis of the sample, the arithmetic device 118 calculates a background intensity corresponding to energy of an analysis line based on a measured intensity of the secondary X-rays that have not been dispersed in the auxiliary measurement area 124 through waveform separation. Further, the arithmetic device 118 performs correction and quantitative analysis, the correction including subtracting a value, which is obtained by multiplying the calculated background intensity corresponding to energy of an analysis line by the ratio stored in advance, from a measured intensity in the main measurement area 122.

It is desired that the sample 103 to be used for calculating the above-mentioned ratio be a reference sample having a known composition. Specifically, for example, the arithmetic device 118 is configured to calculate a background intensity corresponding to energy of an analysis line by performing, for example, waveform separation processing based on a spectrum of the secondary X-rays obtained by measuring the reference sample in a state where the detector 110 is arranged at the position where the secondary X-rays directly enter in the auxiliary measurement area 124. Further, it is more desired that a background intensity corresponding to energy of the analysis line be separated and calculated by directly measuring the spectrum of the background intensity through the use of a reference sample free of elements to be analyzed for which a peak intensity is not required to be separated.

The background intensity measured in the main measurement area 122, with the reference sample being an object to be measured, is calculated, for example, by averaging intensities measured by the detector 110 successively arranged at an equal angle on both sides of a peak angle in the vicinity of a peak of a measurement line. Further, it is more desired that the background intensity be directly measured through the use of a reference sample free of elements to be analyzed.

Next, an operation of the X-ray fluorescence spectrometer according to this embodiment is described. First, description is given of the ratio stored in advance by the storage device 116, for example, in the case of using a reference sample that is essentially free of elements to be analyzed, for example, graphite.

First, a reference sample is irradiated with the primary X-rays in a state where the reference sample is mounted on the sample stage 104. The detector 110 is arranged in the auxiliary measurement area 124 and measures an intensity of the secondary X-rays in a state where the spectroscopic device 120 is retracted.

The intensity of the secondary X-rays measured in this case is higher than that of the dispersed secondary X-rays measured in the main measurement area 122. Therefore, the intensity of the primary X-rays at which the detector 110 is not saturated can also be determined in advance by decreasing a tube current of an X-ray tube that is proportional to the intensity of the primary X-rays. Further, the intensity at which the detector 110 is not saturated may be set by inserting an attenuator having a known attenuation rate into an X-ray optical path.

Then, the counter 112 counts an output pulse signal of the detector 110 as an intensity of the secondary X-rays in accordance with a pulse height corresponding to energy and outputs the measurement result to the arithmetic device 118.

Figure 4:
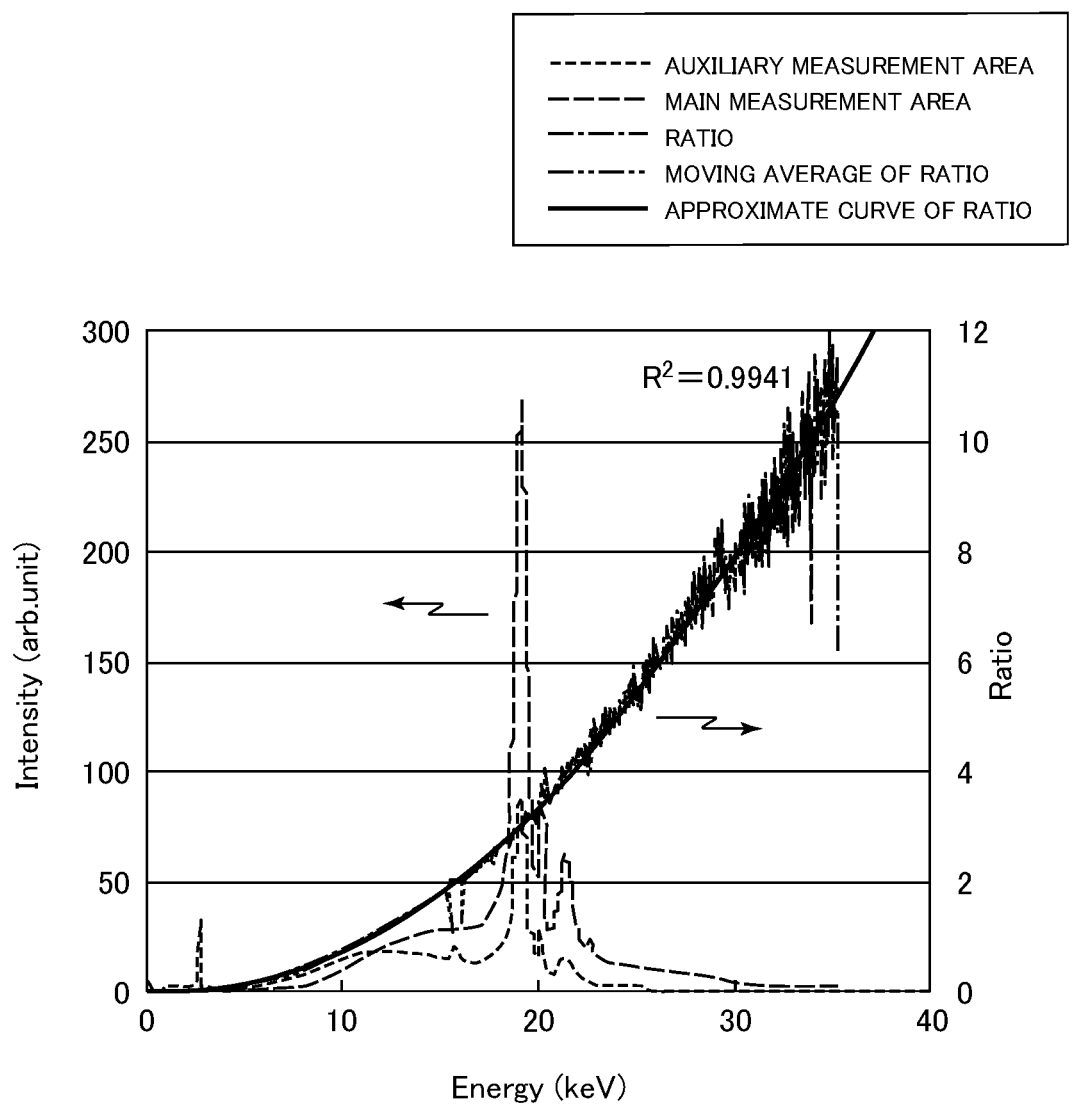
FIG. 4 is a graph for showing an example of calibration curves.

The measurement result output to the arithmetic device 118 is shown in FIG. 4 in a spectrum with the vertical axis representing the intensity of the secondary X-rays and the horizontal axis representing the energy. Specifically, for example, the measurement result in the auxiliary measurement area 124 is a spectrum having a peak intensity of about 90 at an energy of about 19 keV in FIG. 4. The peak of the background spectrum is caused by Compton scattering of the primary X-rays radiated to the sample.

Further, when the reference sample contains, for example, an analytical element, the peak intensity of the contained element is obtained by waveform separation to calculate a background intensity. Specifically, for example, a background intensity with respect to energy is calculated through waveform separation through the use of a least-square method under the assumption that the peak waveform is a Gaussian function and the background intensity is a linear function of energy.

In this case, the detector 110 may be configured to measure an intensity of the secondary X-rays reflected by the total reflection mirror 200 as illustrated in FIG. 2 or may be configured to measure an intensity of the secondary X-rays in a state where the spectroscopic device fixing stage 106 having the spectroscopic device 120 fixed thereto is retracted from a path of the secondary X-rays as illustrated in FIG. 3. When the intensity of the secondary X-rays is measured through the use of the total reflection mirror 200, an unnecessary high energy component contained in the measurement result can be removed. Therefore, the intensity of the secondary X-rays can be efficiently measured with the intensity at which the detector is not saturated in a required energy region.

Next, the scanning mechanism 114 moves the detector 110 to the main measurement area 122. For example, the scanning mechanism 114 moves the detector 110 to a position at which 2θ is 10 degrees. Further, the retracting mechanism 108 places the retracted spectroscopic device 120 at a position where the secondary X-rays enter.

Next, in a state where the reference sample is irradiated with the primary X-rays having an intensity determined in advance, the detector 110 measures an intensity of the secondary X-rays dispersed by the spectroscopic device 120 while the scanning mechanism 114 causes the detector 110 to perform scanning in an area in which 2θ is from 10 degrees to 160 degrees in conjunction with a rotation angle θ of the spectroscopic device 120. The intensity of the secondary X-rays may be successively measured while the scanning of 2θ is stopped for a predetermined period of time for each set step. Further, when there is a limitation on elements to be analyzed, the intensity of the secondary X-rays can also be measured by moving the detector to only a required 2θ angle (energy).

The counter 112 counts an output pulse signal of the detector 110 as an intensity of the secondary X-rays in accordance with 2θ and outputs the result to the arithmetic device 118. Specifically, for example, the measurement result in the main measurement area 122 obtained by converting 2θ to energy by the counter 112 is a spectrum having a peak intensity of about 270 in the vicinity of 19 keV in FIG. 4.

When the reference sample contains, for example, an analytical element, the peak intensity of the contained element is separated to be removed, and a background intensity is calculated. Specifically, for example, a background intensity at a peak angle (energy) is calculated by averaging intensities of the secondary X-rays measured at the same angle on both sides of the peak that does not include the peak intensity under the assumption that the background intensity is a linear function of energy.

Next, the arithmetic device 118 calculates a ratio between the background intensity of the undispersed secondary X-rays measured in the auxiliary measurement area 124 and the background intensity of the dispersed secondary X-rays measured in the main measurement area 122. Specifically, for example, the arithmetic device 118 divides the background intensity of dispersed the secondary X-rays measured in the main measurement area 122 by the background intensity of the undispersed secondary X-rays measured in the auxiliary measurement area 124, to thereby calculate a ratio (vertical axis right scale) corresponding to energy as shown in FIG. 4. As the ratio, for example, a ratio obtained by dividing the background intensity of the undispersed secondary X-rays measured in the auxiliary measurement area 124 by the background intensity of the dispersed secondary X-rays measured in the main measurement area 122 or a relative value with respect to a predetermined value can also be used. Alternatively, for example, a ratio corresponding to a 2θ angle, which is equivalent to energy, may be used.

As shown in FIG. 4, for example, a measured intensity decreases in a high energy region in the auxiliary measurement area 124, and hence the ratio includes a large amount of noise in this region. Thus, it is desired that the ratio be subjected to smoothing processing. In view of the foregoing, the arithmetic device 118 may calculate a moving average as shown in FIG. 4 with respect to the ratio, for example, using a Savitzky-Golay method. When the ratio is calculated only with respect to a 2θ angle (for example, energy of fluorescent X-rays of an analytical element) that is an actual measurement position, the ratio within a certain range centered at the 2θ angle that is the measurement position may be averaged. Further, the smoothing processing may be performed with respect to the background intensities measured in the main measurement area and the auxiliary measurement area before calculation of the ratio.

Further, the arithmetic device 118 may calculate an approximate expression with respect to the moving average of the ratio. Specifically, for example, an approximate curve with respect to the ratio in the measurement result shown in FIG. 4 is represented by the following Expression (1) when a ratio y is a quadratic function of energy x.

$$y = 0.0089x^2 - 0.0017x - 0.118 \quad (1)$$

The square of R shown in FIG. 4 is a so-called determination coefficient and is an indicator representing a degree of coincidence of the approximate expression. As the square of R becomes closer to 1.0, the degree of coincidence becomes higher. The determination coefficient of the approximate curve shown in FIG. 4 is 0.9941.

The secondary X-rays emitted from the sample are attenuated in accordance with a reflection coefficient of the spectroscopic device 120 when the secondary X-rays are dispersed by the spectroscopic device 120. The secondary X-rays measured by the detector 110 in the main measurement area 122 are X-rays dispersed by the spectroscopic device 120. Therefore, the intensity of the secondary X-rays measured by the detector 110 in the main measurement area 122 corresponds to an intensity thereof after being attenuated by the spectroscopic device 120.

Meanwhile, in the auxiliary measurement area 124, the detector 110 directly measures the X-rays output from the sample. Thus, the secondary X-rays measured by the detector 110 in the auxiliary measurement area 124 are not attenuated by the spectroscopic device 120, unlike the secondary X-rays measured by the detector 110 in the main measurement area 122.

Further, the measured intensity of the dispersed secondary X-rays in the main measurement area 122 includes, for example, background intensities of scattered rays in the sample and the fluorescent X-rays emitted from the spectroscopic device, in addition to the analysis line to be used in element analysis. The background intensity at which energy is separated from the analysis line, such as background intensities of the scattered rays by the sample or dispersed higher-order rays, can also be removed by limiting the range of energy to be counted by the counter 112, but the background intensity of X-rays dispersed with the same energy as that of the analysis line cannot be removed.

Thus, the ratio between the background intensity in the main measurement area 122 and the background intensity in the auxiliary measurement area 124 can be calculated as a ratio specific to an optical system, for example, a spectroscopic device, and to measurement conditions. Before the analysis sample is measured, the storage device 116 stores, in advance, the ratio calculated as described above.

It is desired that the storage device 116 be configured to store the ratio corresponding to magnitude of the energy of the secondary X-rays. For example, it is desired that the storage device 116 be configured to store the ratio as a function of the energy of the secondary X-rays. Specifically, as described above, it is desired that the function approximated by a polynomial expression be stored as the ratio.

However, the storage device 116 may store the ratio and energy as a table. Further, the storage device 116 may store only the ratio at a particular energy or within a particular energy range. Further, in the configuration including the plurality of spectroscopic devices 120, the storage device 116 may store the different above-mentioned ratio depending on the spectroscopic devices 120.

Further, it is desired that the sample to be measured be a reference sample free of an element to be analyzed when the above-mentioned ratio is calculated. Specifically, it is desired that the reference sample be, for example, graphite or an acrylic resin. In particular, graphite is less liable to be degraded by irradiation with X-rays, and hence is suitable as the reference sample.

Next, description is given of the processing performed by the X-ray fluorescence spectrometer in the case of measuring the sample 103 to be analyzed in a state where the storage device 116 stores the ratio.

First, the sample 103 to be analyzed is irradiated with the primary X-rays in a state of being mounted on the sample stage 104. Specifically, for example, lead-free solder or a mineral containing lead is mounted on the sample stage 104.

Next, the detector 110 is arranged in the auxiliary measurement area 124. Then, the detector 110 measures an intensity of the secondary X-rays in a state where the spectroscopic device 120 is retracted. Further, the counter 112 counts a pulse signal output from the detector 110 in accordance with a pulse height and outputs the result to the arithmetic device 118.

In this case, the detector 110 may be configured to measure an intensity of the secondary X-rays reflected by the total reflection mirror 200 as illustrated in FIG. 2, or may be configured to measure an intensity of the secondary X-rays in a state where the spectroscopic device fixing stage 106 having the spectroscopic device 120 fixed thereto is retracted from a path of the secondary X-rays as illustrated in FIG. 3.

Next, the scanning mechanism 114 moves the detector 110 to the main measurement area 122. Specifically, for example, the retracting mechanism 108 places the retracted spectroscopic device 120 at a position where the secondary X-rays enter. Further, the scanning mechanism 114 sets the spectroscopic device 120, for example, at an incident angle at which an analysis line of lead is dispersed and moves the detector 110 to a position at which the dispersed analysis line can be measured.

Next, in a state where the sample is irradiated with the primary X-rays, the detector 110 measures an intensity of the secondary X-rays. Further, the counter 112 counts output pulse signals from the detector 110 and outputs the result to the arithmetic device 118.

Next, the arithmetic device 118 performs correction of subtracting the background intensity from the measured intensity in the main measurement area 122. Specifically, for example, the arithmetic device 118 calculates a background intensity corresponding to energy of the analysis line through waveform separation based on the measured intensity in the auxiliary measurement area 124. Then, the arithmetic device 118 multiplies the background intensity by the ratio in the energy of the analysis line corresponding to the position at which the detector 110 is arranged in the main measurement area 122.

In this case, the above-mentioned ratio is a ratio between the background intensities measured in the auxiliary measurement area 124 and the main measurement area 122. Therefore, the value obtained by multiplication can be approximated to the background intensity included in the measured intensity in the main measurement area 122. Next, the arithmetic device 118 performs correction of subtracting the value obtained by multiplication from the measured intensity in the main measurement area 122.

When a combination of measurement conditions differs in the measurement of the reference sample and the sample 103 to be actually analyzed in the main measurement area 122 and the auxiliary measurement area 124, it is required to incorporate such a difference into the ratio or to additionally correct a background intensity to be calculated. For example, when a tube current of an X-ray tube and a measurement time are changed as the measurement conditions, those factors are proportional to the measured intensity of the secondary X-rays and hence can be easily incorporated into the ratio. The same also applies to presence or absence of an attenuator having a known attenuation rate.

The detector 110 is successively moved by the scanning mechanism 114 in accordance with a set analytical element to measure an intensity of the secondary X-rays. Quantitative analysis is performed through the use of the intensity subjected to the above-mentioned correction, thereby calculating a content of the analytical element.

Figure 5:
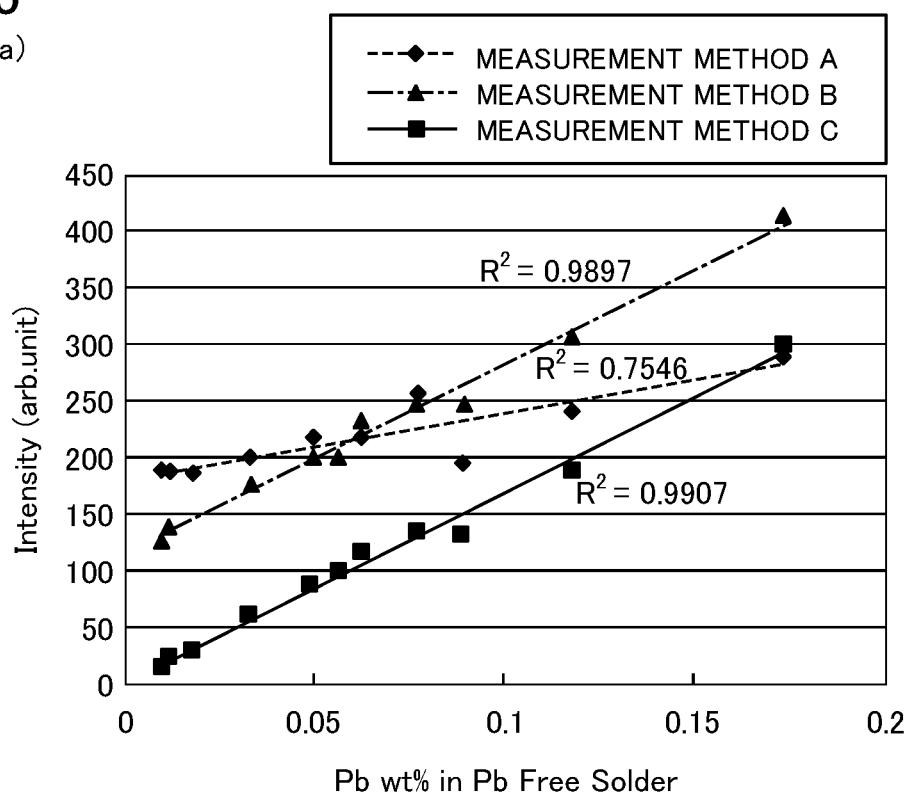
FIGS. 5(A) and (B) are each a graph for showing another example of calibration curves.
Figure 5:
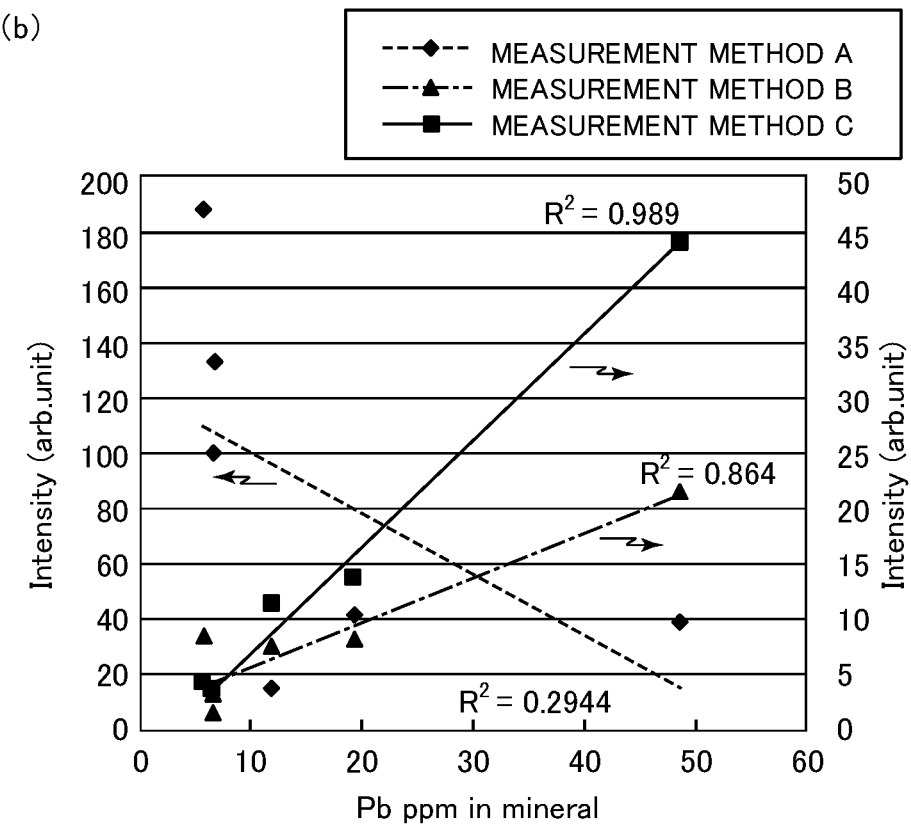

FIG. 5(A) and FIG. 5(B) are each a graph for showing a calibration curve in the case of using the X-ray fluorescence spectrometer according to the present invention and calibration curves in the case of using the related art. 5(A) is a graph for showing calibration curves of lead in the case in which an object to be measured is lead-free solder. The horizontal axis in FIG. 5(A) represents a percentage by mass of lead that is actually contained in a sample being an object to be measured, and the vertical axis in FIG. 5(A) represents an intensity of a PB-1431 line that is an analysis line of lead.

A measurement method A in FIG. 5(A) is a calibration curve in the case of using a wavelength-dispersive X-ray fluorescence spectrometer equipped with a related-art scintillation detector. A measurement method B in FIG. 5(A) is a calibration curve in the case of using a wavelength-dispersive X-ray fluorescence spectrometer, which is equipped with an energy-dispersive detector and removes a background intensity at an energy separated from an analysis line by a related-art method. Further, a measurement method C in FIG. 5(A) is a calibration curve in the case of using the present invention.

The horizontal axis in FIG. 5(A) represents a percentage by mass of lead that is actually contained in the sample being the object to be measured, and hence it is ideal that the intensity of the secondary X-rays at an intercept be 0. However, as shown in FIG. 5(A), in the calibration curves based on the measurement methods A and B, secondary X-rays having a certain intensity are observed even in the case in which an object to be measured is a lead-free sample.

Meanwhile, in the calibration curve based on the measurement method C, the intensity of the secondary X-rays at an intercept is close to 0, and the determination coefficient is also close to 1.0. This shows that high-accuracy quantitative analysis can be performed compared to the related art.

Further, FIG. 5(B) is a graph for showing calibration curves of lead in the case in which an object to be measured is a mineral. The horizontal axis in FIG. 5(B) represents a percentage by mass of lead that is actually contained in the mineral, and the vertical axis in FIG. 5(B) represents an intensity of a PB-L$\beta$1 line that is an analysis line of lead.

A measurement method A in FIG. 5(B) is a calibration curve in the case of using a related-art energy-dispersive X-ray fluorescence spectrometer. A measurement method B in FIG. 5(B) is a calibration curve in the case of using a wavelength-dispersive X-ray fluorescence spectrometer, which is equipped with a scintillation detector and removes a background intensity by a related-art method. Further, a measurement method C in FIG. 5(B) is a calibration curve in the case of using the present invention.

It is desired that the percentage by mass of lead contained in the mineral and the measured intensity of the secondary X-rays have a proportional relationship, and there be less variation with respect to a calibration curve. Thus, it is ideal that the determination coefficient be 1.0.

As shown in FIG. 5(B), when the calibration curve is approximated with a linear function in the measurement methods A and B, the determination coefficient in the measurement method A is 0.2944, and the determination coefficient in the measurement method B is 0.864. Those determination coefficients are values away from 1.0. Therefore, those determination coefficients show that quantitative analysis cannot be performed accurately with the calibration curves based on the measurement methods A and B.

Meanwhile, the determination coefficient based on the measurement method C is 0.989, which is a value close to 1.0. Therefore, this determination coefficient shows that quantitative analysis can be performed accurately with the calibration curve based on the measurement method C.

Here, for ease of understanding, description is given of the example of quantitative analysis using a calibration curve method. However, in principle, the same effects are obtained even through quantitative analysis using a fundamental parameter (FP) method.

As described above, according to the present invention, high-accuracy quantitative analysis can be performed by removing the background intensity, which is calculated based on the intensity of the secondary X-rays measured without being dispersed, from the measured intensity of the secondary X-rays dispersed by the spectroscopic device 120 through the use of the energy-dispersive detector.

Further, when the ratio between the background intensity of the dispersed secondary X-rays and the background intensity of the undispersed secondary X-rays is stored in advance, it becomes unnecessary to move the detector to the vicinity of a peak position to separately perform measurement, and hence prompt measurement can be performed. Further, through continuous movement of the detector 110 between the auxiliary measurement area 124 and the main measurement area 122 by the scanning mechanism 114, a simple configuration can be achieved.

REFERENCE SIGNS LIST

100 X-ray source, 102 sample chamber, 103 sample, 104 sample stage, 106 spectroscopic device fixing stage, 108 retracting mechanism, 110 detector, 112 counter, 114 scanning mechanism, 116 storage device, 118 arithmetic device, 120 spectroscopic device, 122 main measurement area, 124 auxiliary measurement area, 200 total reflection mirror While the above description constitutes the preferred embodiment of the present invention, it will be appreciated that the invention is susceptible to modification, variation and change without departing from the proper scope and fair meaning of the accompanying claims.

The invention claimed is:

1. An X-ray fluorescence spectrometer, comprising:
   an X-ray source configured to irradiate a sample with primary X-rays;
   a spectroscopic element configured to disperse secondary X-rays generated from the sample;
   an energy-dispersive detector configured to measure an intensity of the secondary X-rays;
   a retracting mechanism configured to retract the spectroscopic element from a path of the secondary X-rays;
   a scanning mechanism, which is configured to continuously move the energy-dispersive detector between an auxiliary measurement area for measuring the secondary X-rays in a state where the spectroscopic element is retracted by the retracting mechanism and a main measurement area for measuring the secondary X-rays dispersed by the spectroscopic element, and is configured to change an angle of the spectroscopic element so that the secondary X-rays dispersed by the spectroscopic element enter the energy-dispersive detector in the main measurement area;
   a storage device configured to store, in advance, a ratio between a background intensity of the secondary X-rays measured in the auxiliary measurement area and a background intensity of the secondary X-rays dispersed by the spectroscopic element, which is measured in the main measurement area; and
   an arithmetic device, which is configured to calculate a background intensity included in a measured intensity in the auxiliary measurement area through waveform separation, and is configured to perform correction and quantitative analysis, the correction including subtracting a value, which is obtained by multiplying the calculated background intensity corresponding to energy of an analysis line by the ratio, from a measured intensity of the analysis line in the main measurement area wherein,
   the scanning mechanism continuously and concentrically rotates the energy-dispersive detector between the auxiliary measurement area and the main measurement area so as to share the energy-dispersive detector and the scanning mechanism that are used for measurement in the main measurement area and the energy-dispersive detector and the scanning mechanism that are used for measurement in the auxiliary measurement area.

2. The X-ray fluorescence spectrometer according to claim 1, wherein the scanning mechanism is configured to move the energy-dispersive detector to a position where the secondary X-rays generated from the sample directly enter into the auxiliary measurement area.

3. The X-ray fluorescence spectrometer according to claim 1, further comprising a total reflection mirror, which is configured to remove a high energy component, and is arranged at a position from which the spectroscopic element is retracted,
   wherein the storage device is configured to store, in advance, a ratio between a background intensity of the secondary X-rays reflected by the total reflection mirror, which is measured in the auxiliary measurement area, and a background intensity of the secondary X-rays dispersed by the spectroscopic element, which is measured in the main measurement area.

4. The X-ray fluorescence spectrometer according to claim 1, wherein the spectroscopic element comprises a plurality of spectroscopic elements configured to disperse the secondary X-rays having different wavelengths,
wherein the storage device is configured to store the ratio that varies among the spectroscopic elements.

5. The X-ray fluorescence spectrometer according to claim 1, wherein the storage device is configured to store the ratio corresponding to energy of the secondary X-rays.

6. The X-ray fluorescence spectrometer according to claim 1, wherein the storage device is configured to store the ratio as a function of the energy of the secondary X-rays.

7. The X-ray fluorescence spectrometer according to claim 1, wherein the X-ray fluorescence spectrometer uses a reference sample free of an element to be analyzed when measuring the ratio to be stored in the storage device.

8. The X-ray fluorescence spectrometer according to claim 7, wherein the reference sample comprises graphite or an acrylic resin.

* * * * *